United States Patent
Newmark et al.

(10) Patent No.: US 6,261,607 B1
(45) Date of Patent: Jul. 17, 2001

(54) COMPOSITION FOR PROMOTING PROSTATE HEALTH CONTAINING SELENIUM AND HERBAL EXTRACTS

(76) Inventors: Thomas Newmark, 704 Cordell Ct., St. Louis, MO (US) 63132; Paul Schulick, 222 Kipling Rd., Brattleboro, VT (US) 05301

( * ) Notice: Subject to any disclaimer, the term of this patent is extended or adjusted under 35 U.S.C. 154(b) by 0 days.

(21) Appl. No.: 09/513,186

(22) Filed: Feb. 25, 2000

Related U.S. Application Data

(60) Provisional application No. 60/160,216, filed on Oct. 19, 1999.

(51) Int. Cl.$^7$ ............................. A61K 35/78; A61K 33/04
(52) U.S. Cl. ......................... 424/727; 424/756; 424/758; 424/777; 424/702
(58) Field of Search ........................ 424/195.1, 727, 424/756, 758, 777, 702

(56) References Cited

U.S. PATENT DOCUMENTS

| | | | |
|---|---|---|---|
| 4,843,069 | * 6/1989 | Keller et al. | 514/184 |
| 4,886,665 | * 12/1989 | Kovacs | 424/195.1 |
| 5,002,939 | * 3/1991 | Streber | 514/173 |
| 5,120,558 | 6/1992 | Nguyen et al. | 426/425 |
| 5,264,428 | 11/1993 | Streber | 514/177 |
| 5,543,146 | 8/1996 | Perez | 424/195.1 |
| 5,565,214 | * 10/1996 | Zambo et al. | 424/456 |
| 5,597,550 | * 1/1997 | Mo | 424/40 |
| 5,599,825 | * 2/1997 | Tatsuta et al. | 514/366 |
| 5,763,673 | 6/1998 | Yamazaki et al. | 568/325 |
| 5,858,700 | 1/1999 | Ausich et al. | 435/67 |
| 5,874,084 | 2/1999 | Yng-Wong | 424/195.1 |
| 5,891,440 | 4/1999 | Lansky | 424/195.1 |
| 5,908,628 | 6/1999 | Hou | 424/195.1 |
| 5,910,308 | 6/1999 | D'Jang | 424/195.1 |
| 5,932,101 | 8/1999 | Kanel et al. | 210/634 |
| 6,004,558 | * 12/1999 | Thurn et al. | 424/195.1 |
| 6,039,950 | * 3/2000 | Khwaja et al. | 424/195.1 |

\* cited by examiner

*Primary Examiner*—David M. Naff
*Assistant Examiner*—Mike Meller
(74) *Attorney, Agent, or Firm*—Patton Boggs LLP

(57) ABSTRACT

An herbal composition which can help promote prostate health in men is prepared from saw palmetto, green tea, pumpkin seed oil, ginger, dual urtica root extracts, selenium, watermelon and rosemary. The composition contains therapeutically effective amounts of: supercritical extracts of saw palmetto, ginger, and rosemary, regular or supercritical extracts of green tea, pumpkin seed oil and urtica; selenium; and watermelon. In addition to promoting prostate health, the herbal composition of this invention normalizes urine flow and promotes healthy sexual function and performance. The composition also contains constituents which inhibit 5-lipoxygenase, thereby promoting normal prostate cell growth, and anti-aging constituents that inactivate free radicals, thereby providing antioxidant benefits. The composition is preferably administered orally or parenterally.

15 Claims, No Drawings

COMPOSITION FOR PROMOTING PROSTATE HEALTH CONTAINING SELENIUM AND HERBAL EXTRACTS

This application claims the benefit of Provisional No. 60/160,216 filed Oct. 19, 1999.

BACKGROUND OF THE INVENTION

This invention relates to herbal compositions. More particularly, this invention relates to an herbal composition which can be used to promote healthy prostate function in men. The present invention also relates to methods of using such compositions to promote prostate health.

In men, the prostate gland is the source of several common disorders including prostatitis and benign prostatic hypertrophy (BPH), wherein the prostate gland becomes inflamed or enlarged. BPH can cause many uncomfortable and annoying symptoms including: difficulty in starting to urinate; increased urge to urinate; a weak or interrupted stream when urinating; a feeling that the bladder cannot be emptied completely; a feeling of decay when urination is started; a need to urinate often, especially at night; and frequent or continuous lower back pain.

Drug therapies exist which can help offset some of the symptoms of BPH but these are associated with significant side effects such as, e.g., impotence.

Recent scientific studies, including one published in the *Proceedings of the National Academy of Sciences*, demonstrate that the enzyme, 5-lipoxygenase (5-LO), is specifically involved in prostate cancer cell proliferation. Inhibition of this enzyme can lead to massive and rapid apoptosis of prostate cancer cells. Drugs are being developed which inhibit 5-LO and prostate cancer cell proliferation. Unfortunately, these drugs can have significant side effects, including, e.g., eosinophilia, compromised liver function, and cardiomyopathy.

Herbs like saw palmetto and nettle have been associated with relief of BPH symptoms but these herbs have not been commercially identified as 5-LO inhibitors or for the application of reducing prostate cancer cell proliferation.

Research from databases combing international studies indicates that ginger contains the highest number of constituents which can inhibit 5LO. See also, e.g., U.S. Pat. No. 5,763,673; *Chem Pharm Bull* (Tokyo) 1992 Feb;40(2):387-91 *Inhibition of prostaglandin and leukotriene biosynthesis by gingerols and diarylheptanoids*, Kiuchi, F, Iwakani S, Shibuya M, Hanaoka F, Sankawa U Faculty of Pharmaceutical Sciences, University of Tokyo, Japan; and Nippon Yakurigaku Zasshi 1986 Oct.;88(4):263-9 [*Pharmacological studies on ginger, IV, Effect of (6)-shogaol on the arachidonic cascade*].Suekawa M, Yuasa K, Isono M, Sone H, Ikeya Y, Sakakibara I, Aburada M, Hosoya E.

Olive oil also possesses the ability to inhibit 5-LO. See, e.g., *Biosci Biotechnol Biochem* 1997 Feb;61(2).347-50 *Inhibition of arachidonate lipoxygenase activities by 2–(3, 4–dihydroxyphenyl)ethanol, aphenolic compound from olives*. Kohyana N, Nagata T, Fujimoto S, Sekiya K Shikoku National Agricultural Experiment Station, Kagawa, Japan; and *Biochem Pharmacol* 1999 Feb 15;57(4):445-9 *Inhibition of leukocyte 5-lipoxygenase by phenolics from virgin olive oil*, de la Puerta R, Ruiz Gutierrez V, Hoult J R Pharmacology Group, King's College London, UK.

Ursolic acid and carnosol, constituents in rosemary, have also been determined to be inhibitors of 5-LO. See, e.g., *Biochim Biophys Acta* 1992 Apr 8;1125(1):68–72 *Inhibition of lipoxygenase activity and HL60 leukemic cell proliferation by ursolic acid isolated from heather flowers (Calhora vulgaris)*. Simon A, Najid A, Chulia A J, Delage C, Rigaud M *CJF INSERM* 88-03, Faculte de Medecine, Limoges, France; and *Biochem Pharmacol* 1991 Oct 9;42(9); 1673–81 *Inhibition of mammaliam 5-lipoxgenase and cydo-oxgenase by flavnoids and phenolic dietary additives. Relationship to antioxidant activity and to iron ion-reducing ability*. Laughton M J, Evans P J, Moroney M A, Hoult J R, Halliwell B Department of Biochemistry, King's College London, U.K.

As mentioned hereinabove, saw palmetto also has been found to possess 5-ipoxygenase-inhibiting abilities. See, e.g., *Arzneimittelforschung* 1992 Apr;42(4):547–51[Anti-inflammatory activity of sabal fruit extracts prepared with supercritical carbon dioxide. In vitro antagonists of cydoxygenase and 5-lipoxygnease metabolism]. Breu W, Hagenlocher M, Redl K, Tittel G, Stadler F, Wagner H Institut fur Pharmazeutische Biologie, Ludwig-Maximilians-Universitat Munchen; and *Prostaglandins Leukot Essent Fatty Acids* 1997 Sep;57(3):299–304 *Effect of the lipidic lipidosterolic extract of Serenoa repens(Permixon) on the ionophore A23187-stimulated production of leukotriene B4 (LTB4) from human polymorphonuclear neutrophils*. Paubert-Braquet M, Mencia Hueta JM, Cousse H, Braquet P Bio-Inova, Life Sciences International, Plaisir, France.

Nettle root extract and its phenolic components caffeic acid are also inhibitors of 5-lipoxygenase. See, e.g., Arznei-mittelforschung 1996 Jan;46(1):52–6 [*Anti-inflammatory effect of Urtica diaica folia extract in comparison to caffeic malic acid*]. Obertreis B, Giller K, Teucher T, Behnke B, Schmitz H Strathmann A G, Hamburg.

Other references which teach the use of herbs to relieve symptoms associated with various prostate disorders (including, e.g., prostate enlargement, benign prostatic hyperplasia, and prostate cancer) is disclosed, for example, in U.S. Pat. Nos. 5,543,146; 5,264,428; 5,910,308; and 5,858,700.

It is continually desirable to provide alternative herbal compositions which are capable of promoting not only prostate health (including normal prostate cell growth) but also healthy sexual functioning and performance and antioxidant activity.

A primary object of this invention is to provide an herbal composition which is capable of inhibiting 5-lipoxygenase, thereby promoting normal cell activity and vitality in the prostate gland and thus significantly supporting prostate health.

A further object of this invention is to provide an herbal composition which, in addition to promoting prostate health, also promotes healthy sexual functioning and performance and provides antioxidant benefits.

A still further object of this invention is to provide an orally or parenterally administered herbal composition capable of providing the therapeutic benefits recited in the preceding objects.

Another object of this invention is to provide methods of promoting prostate health in men, using an herbal composition having the characteristics set forth in the preceding objects.

These and other objects are achieved in the present invention.

SUMMARY OF THE INVENTION

The present invention provides a unique formation which is designed to provide an herbal polyphytonutrient approach to the inhibition of 5-lipoxygenase and the promotion of prostate health in men.

The herbal composition of the present invention contains extracts taken from saw palmetto, green tea, pumpkin seed oil, ginger, dual urtica root extracts, selenium, watermelon and rosemary. More specifically, the herbal composition of this invention contains therapeutically effective amounts of supercritical extracts of saw palmetto, ginger, and rosemary, and either regular or supercritical (preferably regular) extracts of green tea, pumpkin seed oil, and urtica root. The composition further contains selenium and watermelon. In preferred embodiments of the present invention, the ginger supercritical extract is a supercritical extract of certified organic ginger.

In addition to promoting prostate health, the herbal composition of this invention normalizes urine flow, promotes healthy sexual function and performance and scavenges oxygen free radicals, thereby exhibiting antioxidant activity.

Another novel feature of the present invention is that supercritical-solvent free extraction technology is used in association with 5-lipoxygenase inhibition. This technology allows for highest potency of active compounds, as much as 250 times the potency of original fresh plant material.

DETAILED DESCRIPTION OF THE INVENTION

As stated above, the present invention provides an herbal active-ingredient composition capable of promoting prostate health in men.

The active-ingredient herbal composition contains extracts taken from saw palmetto, green tea, pumpkin seed oil, ginger, urtica, and rosemary, and further contains selenium and watermelon. As used herein, the term "extract" is intended to mean a concentrate of water-soluble and/or alcohol-soluble plant components from the portion of the plant extracted and can be in aqueous or powdered form. In the present invention, the extracts from saw palmetto, ginger, and rosemary are obtained using a supercritical extraction process as discussed later herein. Accordingly, these extracts are referred to herein as "supercritical extracts". The extracts from green tea, pumpkin seed oil, and urtica can be prepared using either a supercritical extraction process or a conventional extraction process. If prepared using a conventional extraction process, the extracts will be referred to herein as "regular extracts" as a means of distinguishing these extracts from the supercritical extracts. In preferred embodiments of the present invention, regular extracts of the green tea, pumpkin seed and urtical are used.

Saw palmetto (Serenoa repens) effectively reduces the size of the enlarged prostate and restores function. The saw palmetto berry contains an oil composed of sterols and various saturated and unsaturated fatty acids. In Europe and now in the United States, the purified fat soluble extract from the saw palmetto berry is used medicinally.

Green tea contains 51 anti-inflammatory phytonutrients with critical anti-aging and prostate-specific health benefits. The main biologically active ingredients in green tea are polyphenols. Green tea polyphenols have been shown to prevent cancers of the prostate, lung, breast, liver, skin, esophagus, and colon. In the present invention, the green tea extract is preferably taken from the leaf of the plant.

Pumpkin seed oil also has a beneficial effect on the enlarged prostate.

Ginger is a rich herbal source of 5-lipoxygenase inhibitors. In the present invention, the ginger supercritical extract is preferably taken from the rhizome of the plant. In the most preferred embodiments of the present invention, the ginger supercritical extract is the supercritical extract of certified organic ginger.

The composition of the present invention uses two extracts of urtica, one of which is a hydroalcoholic extract and the other of which is an aqueous exact. The two extracts provide the fullest spectrum of anti-inflammatory prostate-specific phytonutrients, with demonstrated clinical benefit in conjunction with saw palmetto. The extracts are preferably taken from the roots of the urtica plant.

Selenium is a trace nutrient that is critical to tissue detoxification and long term prostate health.

Watermelon is a rich source of lycoprene complex, a celebrated prostate-specific anti-aging nutrient.

The rosemary supercritical extract contains numerous anti-aging constituents and significant 5-lipoxygenase inhibitors. The extracts are preferably taken from the leaf and essential oil of the plant.

As stated hereinabove, the active ingredient composition of this invention contains the supercritical extracts of saw palmetto, ginger, and rosemary. Supercritical extraction of these herbs can be carried out according to known supercritical detraction methods. Such methods are disclosed, e.g., in U.S. Pat. Nos. 5,932,101 and 5,120,558, which are hereby incorporated by reference herein.

U.S. Pat. No. 5,932,101 discloses a supercritical extraction process wherein an extraction solvent and a fluid feed are supplied with a countercurrent flow to an extraction column. The extraction solvent contains a dense gas (e.g., carbon dioxide), and the fluid feed contains at least one solute (e.g., an herb) and a carrier fluid (e.g., water). The solute is selective to the extraction solvent with respect to the carrier fluid. The carrier fluid contains at least one component which is barely soluble in the extraction solvent and substantially immiscible with the extraction solvent so as to provide two phases. The fluid feed and the extraction solvent intimately contact one another in the column for a sufficient amount of time to extract the solute from the carrier fluid to the extraction solvent. The column operates in an enhanced solubility region having a pressure of between 450 and 1200 bar and a temperature of between 50° C. and 300° C. The column has a diameter greater than about 3.5 centimeters and a height to diameter ratio of greater than about 5. A raffinate containing the carrier fluid is removed from the column, as is an extract containing the extraction solvent and the solute. The combination of pressure and temperature is sufficient for the solubility of the solute in the extraction solvent to be at least 250% by weight greater than the solubility of the solute in the extraction solvent at the same operating temperature but at 200 bar pressure. Additionally, the solute may be separated from the extraction solvent in a phase separation device such as a decanter, a coalescer, a cyclone and a second extraction column.

The supercritical extraction process disclosed in U.S. Pat. No. 5,120,558 involves grinding a spice or herb and then extracting the ground spice or herb with supercritical fluid carbon dioxide under a pressure of from about 400 bar to about 600 bar and at a temperature of from about 80° C. to about 120° C. At least one oleoresin fraction is precipitated from the loaded supercritical fluid under a pressure of from about 280 bar to about 380 bar and at a temperature of from about 80° C. to about 100° C. Additional oleoresins may be obtained by next adjusting the pressure of the supercritical fluid to from about 100 bar to about 200 bar within the same temperature range of 80° C. to 100° C., and finally by reducing the pressure to from about 30 bar to about 50 bar and the temperature to from about 0° C. to about 30° C.

The green tea, pumpkin seed oil, and urtica, extracts used in the present invention can be prepared using either conventional or supercritical extraction techniques. Preferably, the extracts of these herbs used in the present invention are regular extracts. Suitable conventional extraction techniques are disclosed, e.g., in U.S. Pat. Nos. 5,891,440; 5,874,084; and 5,908,628; all of which are hereby incorporated by reference herein.

For example, the green tea, pumpkin seed oil, and urtica extracts used in the herbal composition of this invention can be prepared by contacting the herb with an appropriate solvent to form the extract. To make the extract suitable for oral administration, the solvent used must be substantially non-toxic to the subject so that there is no untoward level of adverse side effects, such as toxicity, irritation, allergy or hypersensitivity responses. The level of any such side effects should be commensurate with acceptable risk/benefit ratios. Examples of such substantially nontoxic solvents include water and ethanol.

In one extraction method which can be used herein, the plant portion to be extracted is placed into an extractor, 70% ethanol is added, and the resultant mixture is heated under reflux. Ethanol is recovered and condensed under low temperature and decompression until the specific density reaches 1.38 (thermal assay). The extract is then collected by vacuum drying.

The herbal composition of this invention can be prepared, for example, by individually washing, drying and grinding the herbs into fine powder, and then extracting the ground herbs (via supercritical extraction in the case of saw palmetto, ginger, and rosemary, and via either supercritical extraction or conventional extraction for green tea, pumpkin seed oil, and urtica). The resulting extracts are then mixed together with selenium and watermelon (preferably in freeze-dried form) in amounts that are physiologically acceptable to the patient. No special mixing means is required. The mixture of extracts can be encapsulated, tableted or formulated with a physiologically acceptable vehicle into unit dosages.

The herbal active ingredient composition of this invention contains therapeutically effective amounts of the herbal extracts, selenium and watermelon. As used herein, the term "therapeutically effective amount" means that amount which, in conjunction with the amounts of the other ingredients present in the composition, will provide a composition capable of promoting prostate health in men.

The herbal composition of this invention can be administered orally or parenterally (e.g., by intravenous drip or by intraperitoneal, subcutaneous or intramuscular injection). Most preferably, the composition of this invention is administered orally.

The orally administered embodiments of the herbal composition of this invention can be in any conventional form such as, e.g., capsules (hard or soft), tablets, elixirs, powders, granules, suspensions in water or non-aqueous media, sachets, as additives to food or beverages, or even can be made into a tea. Most preferably, the orally administered embodiment of the composition is in the form of a soft gel capsule which is swallowed with water.

For preparing solid orally administered compositions such as capsules or tablets, the principal active ingredients are mixed with a pharmaceutical carrier (e.g., conventional tableting ingredients such as corn starch, lactose, sucrose, sorbitol, talc, stearic acid, magnesium stearate, dicalcium phosphate or gums) and other pharmaceutical diluents (e.g., water) to form a solid preformulation composition containing a substantially homogenous mixture of the composition of this invention, or a non-toxic pharmaceutically acceptable salt thereof. When referring to the preformulation compositions as substantially homogenous, it is meant that the active ingredients are dispersed evenly throughout the composition so that the composition may be readily subdivided into equally effective unit dosage forms such as capsules, pills and tablets. This solid preformulation composition can then be subdivided into unit dosage forms containing, for example, from 0.15 to 1.0 gram, of the active-ingredient composition.

Liquid preparations for oral administration may take the form of, for example, solutions, syrups or suspensions, or they may be presented as a dry product for reconstitution with water or other suitable vehicles before use. Such liquid preparations may be prepared by conventional means with pharmaceutically acceptable additives such as suspending agents (e.g., sorbitol syrup, methyl cellulose, or hydrogenated edible fats); emulsifying agents (e.g., lecithin or acacia); non-aqueous vehicles (e.g., almond oil, oily esters or ethyl alcohol); preservatives (e.g., methyl or propyl p-hydroxybenzoates or sorbic acid); and artificial or natural colors and/or sweeteners.

The active compounds may be formulated for parenteral administration by injection, which includes using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as stabilizing, suspending or dispersing agents. Alternatively, the active ingredients may be in powder form for reconstitution with a suitable vehicle, e.g., sterile pyrogert-free water, before use.

The active-ingredient composition of this invention can be combined with the physiologically acceptable vehicle into unit dosages. A unit dosage can comprise a therapeutically effective amount of each active ingredient for a single daily administration (e.g., orally), or it can be formulated into smaller quantities of each ingredient to provide for multiple doses in a day. A unit dosage will depend upon many factors including age, size, and condition of the patient being treated and the number of times the unit will be taken in a single day. In any event, the entire daily dosage will be that which is physiologically acceptable to an individual and can be administered daily over a prolonged period of time. In the present invention, normally between about 300 and 2000 mg of the active-ingredient composition is orally administered per day, with part of the total dose preferably taken at two or more different times during the day. of the extracts used in the composition of this invention will depend active ingredients found naturally in each component. Using the guidance a basic knowledge of drug preparation and pharmacology, one skilled in the art could easily adjust the proportions of the separate components of the composition so as to obtain a composition which has the therapeutic effects discussed herein.

The present invention is also directed to methods of promoting prostate health in men, involving orally or parenterally administering an effective amount of the active-ingredient composition of this invention to a man. The term "effective amount" with respect to the active-ingredient composition means that amount sufficient to promote prostate health. The effective amount will depend on the extent of prostate disorder and on the responsiveness of the patient to the composition. Persons of ordinary skill in the art can easily determine optimum dosages, dosing methodologies and repetition rates.

Suitable modes of parenteral administration include, e.g., intravenous drip; intraperitoneal, subcutaneous or intramuscular injection; and the like.

Oral administration is accomplished by ingesting the composition. As stated previously herein, the most preferred form of the orally administered composition of this invention is the soft gel capsule, which is preferably swallowed with water.

Presented in the table below is a particularly preferred embodiment of the orally administered soft gel capsule form of the composition of this invention. The formulation below is the combined compositions of two soft gel capsules. In other words, two capsules constitute a single serving or unit dose of two capsules. In other words, two capsules constitute a single serving or unit dose of the composition. Each capsule contains a portion of the overall composition.

TABLE

Orally Administered Composition:
Formulation Per Serving (Two Capsules)

| Ingredient | Amount |
| --- | --- |
| Saw Palmetto, berry, supercritical extract (85–95% total fatty acids-272–304 mg) | 320 mg |
| Green Tea, leaf, extract (45% polyphenols-45 mg) | 100 mg |
| Pumpkin Seed Oil, certified organic | 96 mg |
| Ginger, rhizome, certified organic, supercritical extract (minimum 20% pungent compounds-16 mg, 5% zingiberene-4 mg) | 80 mg |
| Urtica root extract, aqueous alcoholic, 10:1 | 50 mg |
| Urtica root extract, aqueous, 5:1 | 50 mg |
| Selenium (Bio-Grown ™) | 50 mcg |
| Watermelon, fruit, freeze-dried | 50 mg |
| Rosemary, leaf & essential oil, supercritical extract (23% total phenolic antioxidants [TPA]-2.3 mg) | 10 mg |

The composition set forth in the table above preferably her contains olive oil (certified organic) and yellow beeswax.

The soft gel capsules containing the composition set forth in the table above are preferably composed of gelatin, vegetable glycerine, purified water and carob.

For oral administration of the above-recited formulation, two soft gel capsules (together constituting one serving) are preferably taken daily, with 8 ounces of water.

What is claimed is:

1. An orally administered composition for promoting prostate health in males, comprising amounts therapeutically effective to promote said prostate health of selenium, supercritical carbon dioxide extracts of saw palmetto berry, ginger, and rosemary leaf and aqueous, alcoholic, aqueousalcoholic or supercritical carbon dioxide extracts of green tea leaf, pumpkin seed oil, and urtica root.

2. A composition according to claim 1, further comprising watermelon.

3. A composition according to claim 1, wherein the ginger is certified organic ginger.

4. A composition according to claim 1, wherein the orally administered composition is in a form selected from the group consisting of capsules, tablets, elixirs, powders, granules, suspensions, sachets, food additives, beverage additives, and tea.

5. A composition according to claim 4, wherein the orally administered composition is in the form of two soft gel capsules, the two capsules in combination comprising: about 320 milligrams of a supercritical carbon dioxide extract of saw palmetto berry, about 100 milligrams of a green tea leaf aqueous, alcoholic or aqueousalcoholic extract; about 96 milligrams of certified organic pumpkin seed oil; about 80 milligrams of a supercritical carbon dioxide extract of a certified organic ginger rhizome; about 50 milligrams of a aqueousalcoholic urtica root extract; about 50 milligrams of an aqueous urtica root extract; about 50 micrograms of selenium; about 50 milligrams of freeze-dried watermelon; and 10 milligrams of a supercritical carbon dioxide extract of rosemary leaf.

6. A composition according to claim 5, wherein the saw palmetto berry supercritical carbon dioxide extract contains from about 85% to about 95% by weight total fatty acids; the green tea leaf extract contains about 45% by weight polyphenols; the ginger supercritical carbon dioxide extract contains at least 20% by weight of pungent compounds and about 5% by weight of zingiberene; and the rosemary leaf supercritical carbon dioxide extract contains about 23% by weight of phenolic antioxidants.

7. A composition according to claim 5, further comprising olive oil, yellow beeswax, gelatin, glycerine, purified water, and carob.

8. A composition according to claim 1, wherein the composition is a parenterally administered composition.

9. A method of promoting prostate health in a male, comprising orally administering to said male a composition comprising amounts therapeutically effective to promote said prostate health, of selenium, supercritical carbon dioxide extracts of saw palmetto berry, ginger, and rosemary leaf and aqueous, alcoholic, or aqueousalcholic supercritical carbon dioxide extracts of green tea leaf, pumpkin seed oil, and urtica root.

10. A method according to claim 9, wherein the composition further comprises watermelon.

11. A method according to claim 9, wherein the ginger is certified organic ginger.

12. A method according to claim 9, wherein the orally administered composition is in a form selected from the group consisting of capsules, tablets, elixirs, powders, granules, suspensions, sachets, food additives, beverage additives, and tea.

13. A method according to claim 12, wherein the orally administered composition is in the form of two soft gel capsules, the two capsules in combination comprising: about 320 milligrams of a supercritical carbon dioxide extract of saw palmetto berry, about 100 milligrams of a green tea leaf aqueousalcoholic extract; about 96 milligrams of certified organic pumpkin seed oil; about 80 milligrams of a supercritical carbon dioxide extract of a certified organic ginger rhizome; about 50 milligrams of a aqueousalcoholic urtica root extract; about 50 milligrams of an aqueous urtica root extract; about 50 micrograms of selenium; about 50 milligrams of freeze-dried watermelon; and 10 milligrams of a supercritical carbon dioxide extract of rosemary leaf.

14. A method according to claim 13 wherein the saw palmetto berry supercritical carbon dioxide extract contains from about 85% to about 95% by weight total fatty acids; the green tea leaf extract contains about 45% by weight polyphenols; the ginger supercritical carbon dioxide extract contains at least 20% by weight of pungent compounds and about 5% by weight of zingiberene; and the rosemary leaf supercritical carbon dioxide extract contains about 23% by weight of phenolic antioxidants.

15. A method according to claim 14, wherein the two soft gel capsules are administered to said male on a daily basis.

* * * * *